US00PP18323P3

(12) United States Plant Patent

Miyano et al.

(10) Patent No.: US PP18,323 P3

(45) Date of Patent: Dec. 18, 2007

(54) *PETUNIA* PLANT NAMED 'KEIPUNES'

(50) Latin Name: *Petunia hybrida* Vilm
Varietal Denomination: Keipunes

(75) Inventors: Shinya Miyano, Katori-gun (JP); Kazunari Iwaki, Omihachiman (JP)

(73) Assignees: Suntory Flowers Limited, Tokyo (JP); Keisei Rose Nurseries, Inc., Tokyo (JP)

( * ) Notice: Subject to any disclaimer, the term of this patent is extended or adjusted under 35 U.S.C. 154(b) by 21 days.

(21) Appl. No.: 11/409,912

(22) Filed: Apr. 24, 2006

(65) Prior Publication Data

US 2007/0250975 P1 Oct. 25, 2007

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent Bell
*Assistant Examiner*—Annette H Para
(74) *Attorney, Agent, or Firm*—Jondle & Associates, P.C.

(57) ABSTRACT

A new *petunia* plant particularly distinguished by abundant, small, vivid red-purple flowers, abundant branching with a great profusion of blooms, excellent tolerance to rain and a vigorous, decumbent growth habit is disclosed.

2 Drawing Sheets

Genus and species: *Petunia hybrida* Vilm.
Variety denomination: 'Keipunes'.

BACKGROUND OF THE NEW PLANT

The present invention comprises a new and distinct cultivar of *petunia,* botanically known as *Petunia hybrida* Vilm., and hereinafter referred to by the cultivar name 'Keipunes'. The new cultivar originated from a hybridization made in October 2000 in Katori, Chiba, Japan. The female parent was a proprietary unnamed *petunia* plant (unpatented), while the male parent was a different proprietary unnamed *petunia* plant (unpatented).

The new cultivar was created in 2000 in Katori, Chiba, Japan and has been asexually reproduced repeatedly by vegetative cuttings in Katori, Chiba, Japan. The present invention has been found to retain its distinctive characteristics through successive asexual propagations.

Plant Breeder's Rights for this cultivar were applied for in Switzerland on Jul. 20, 2005, in Norway on Jan. 12, 2006 and with the European Union on Feb. 20, 2006.

SUMMARY OF THE INVENTION

The following are the most outstanding and distinguishing characteristics of this new cultivar when grown under normal horticultural practices in Katori, Chiba, Japan.

A) Abundant, small-size, vivid red-purple flowers;

B) Abundant branching with a great profusion of blooms;

C) Vigorous, decumbent growth habit;

D) Excellent tolerance to rain; and

E) Whole plant remains in bloom for a considerable period of time.

DESCRIPTION OF PHOTOGRAPHS

This new *petunia* plant is illustrated by the accompanying photographs which show blooms and foliage of the plant in full color, the colors shown being as true as can be reasonably obtained by conventional photographic procedures. The photographs are of a 2-month-old plant grown in a greenhouse in Katori, Chiba, Japan.

DESCRIPTION OF THE NEW CULTIVAR

Figure 1:
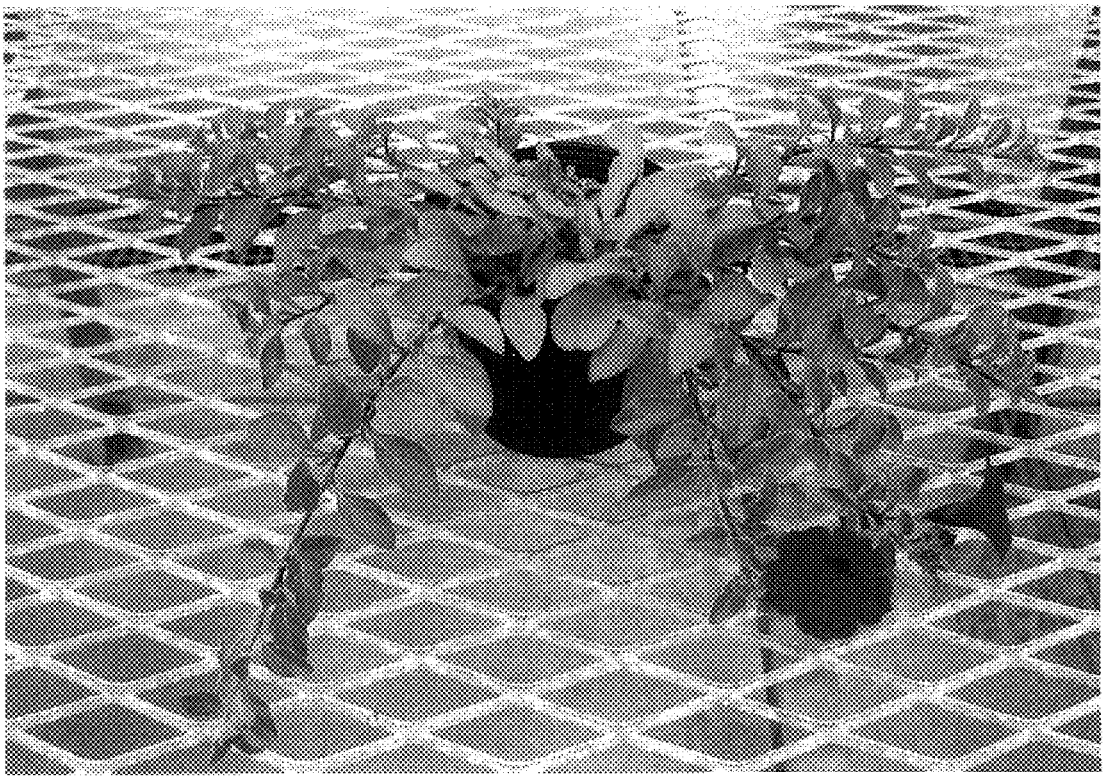
FIG. 1 shows the overall plant habit, including blooms, buds and foliage.
Figure 2:
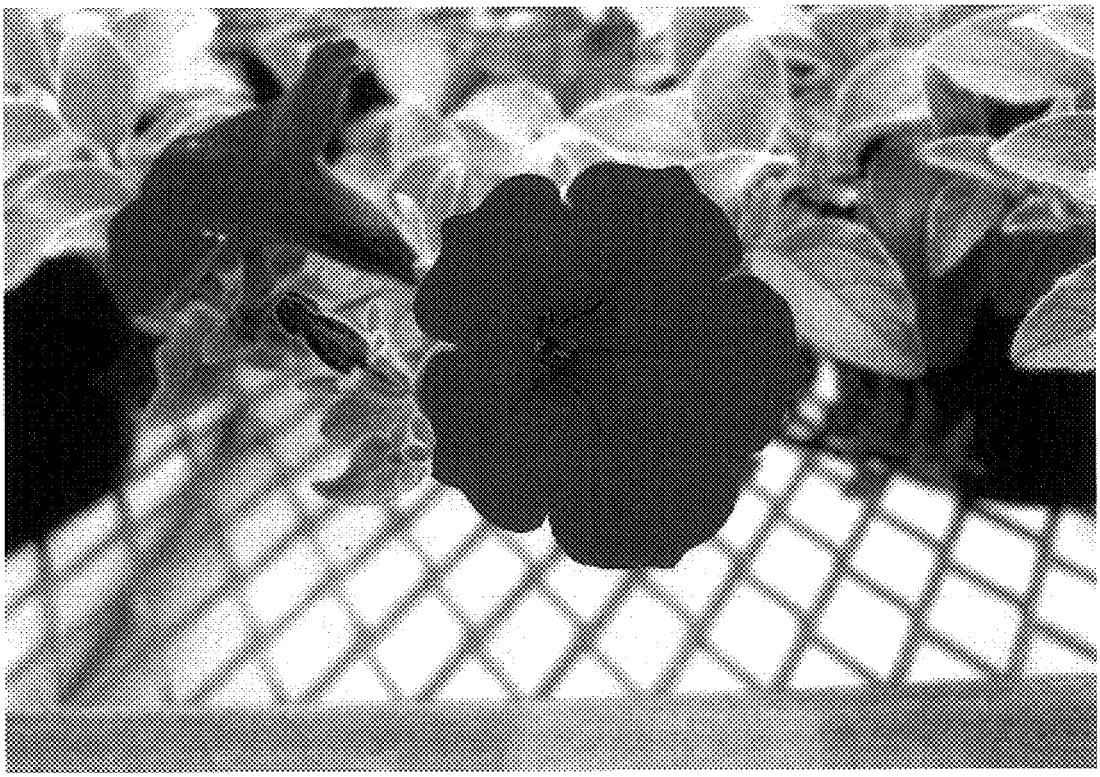
FIG. 2 shows the mature flower.

The following detailed description sets forth the distinctive characteristics of 'Keipunes'. The data which define these characteristics were collected from asexual reproductions carried out in Katori, Chiba, Japan. The plant history was taken on 2-month old plants which were planted as rooted cuttings in 12-cm pots in 2005 and grown in a greenhouse between 18° C. and 25° C. The plants were pinched once in September 2005. Observations were made when the plants were in full flower in October 2005. Color readings were taken under natural light in the greenhouse. Color references are primarily to The R.H.S. Colour Chart of The Royal Horticultural Society of London (R.H.S.) (2001).

DETAILED BOTANICAL DESCRIPTION

Classification:
- *Family.*—Solanaceae.
- *Botanical.*—*Petunia hybrida* Vilm.
- *Common name.*—*Petunia.*

Parentage:
- *Female parent.*—An unnamed proprietary red-purple (RHS 74B) flowered *petunia* plant (unpatented).
- *Male parent.*—An unnamed proprietary red-purple (RHS 74A) flowered *petunia* plant (unpatented).

Growth:
- *Form.*—Annual.
- *Habit.*—Decumbent to trailing shape, freely branching, vigorous.

*Height* (*measured from the top of the soil*).—5.0 cm.
*Diameter or area of spread.*—30.0 cm.
*Propagation.*—Terminal tips for cutting.
*Time to produce a finished flowering plant.*—2 to 3 weeks, in late April to late September, for a 12-cm pot.
*Keeping quality.*—210 days.
*Outdoor plant performance.*—Use in hanging baskets and containers; ground cover; excellent tolerance to rain; normal tolerance to wind.
*Time to initiate and develop roots.*—7 days at 20° C. to 25° C.
*Time to produce rooted cutting or liner* (*young plant*).—21 days at 20° C. to 25° C.
*Root description.*—Light brown, fibrous, fine; fleshy, freely-branching.

Branches:
*Number of branches.*—1 basal branch; many lateral branches.
*Length of lateral branches.*—15.0 cm.
*Diameter of lateral branches.*—0.2 cm.

Stems:
*Description.*—Round in cross-section.
*Aspect.*—Lying flat and apex ascended.
*Color.*—RHS 137B.
*Diameter.*—0.2 cm.
*Stem length.*—15.0 cm.
*Internode length.*—2.5 cm.
*Anthocyanin.*—Present.
*Texture.*—Pubescent.

Leaves:
*Arrangement.*—Alternate, single leaves, abundant.
*Apex.*—Obtuse.
*Base.*—Cuneate.
*Color* (*mature leaves*).—Upper surface: RHS 137B. Lower surface: RHS 137C.
*Color* (*immature leaves*).—Upper surface: RHS 137B. Lower surface: RHS 137C.
*Margin.*—Entire.
*Size.*—Length: 4.5 cm. Width: 1.5 cm.
*Shape.*—Elliptical.
*Texture.*—Viscid, pubescence on both sides.
*Venation type.*—Reticulate.
*Petiole.*—Not clearly distinct from the leaf blade.

Flower buds:
*Color.*—RHS 79B.
*Shape.*—Cylindrical.
*Size.*—Length: 1.5 cm. Diameter: 0.5 cm.

Inflorescence:
*Blooming habit.*—Continuous.
*Inflorescence type.*—Single flower; self-cleaning.
*Arrangement.*—Borne in upper leaf axils.
*Aspect.*—Upright to outward.
*Shape.*—Funnel-shape with five lobes; petals fused.
*Fragrance.*—Faint.
*Flower number* (*per inflorescence.*).—One.
*Quantity of flowers and buds per plant.*—Abundant.
*Flower longevity on plant.*—4 days.
*Peduncle.*—Color: RHS 144B. Length: 1.5 cm. Diameter: 0.1 cm. Texture: Pubescent, viscid.

Flowers:
*Size.*—Height (flower depth): 4.0 cm. Diameter: 4.5 cm.
*Corolla.*—Shape: Tube. Color (outside): RHS 83B with RHS 79B venation.
*Petals.*—Shape: Very broadly obtrullate. Size: Length (from the throat): 3.0 cm. Width: 1.5 cm. Apex: Cuspidate. Base: Fused. Margin: Entire, weakly undulated. Color (when opening): Upper surface: RHS 74B. Lower surface: RHS 83B. Color (fully opened): Upper surface: RHS 74B. Lower surface: RHS 83B. Throat color (inside): RHS 83B with RHS 79B venation. Petal texture: Upper surface: Satiny. Lower surface: Satiny.
*Calyx.*—Form: Tubular, star-shape. Length: 1.0 cm. Diameter: 2.0 cm.
*Sepals.*—Number: 5. Shape: Narrowly oblong, bent over outwardly. Apex: Round. Base: Fused. Margin: Entire. Size: Length: 1.0 cm. Width: 0.2 cm. Color (mature): Upper surface: RHS 144A. Lower surface: RHS 144B. Color (immature): Upper surface: RHS 144A. Lower surface: RHS 144B.

Reproductive organs:
*Stamens.*—Quantity: 5. Anther: Shape: Ellipsoidal. Size: Length: 0.2 cm. Width: 0.1 cm. Color: RHS 92B.
*Pollen.*—Amount: Normal. Color: RHS 92C.
*Pistil.*—Quantity: One. Length: 1.5 cm.
*Style.*—Length: 1.0 cm. Color: RHS 154D.
*Stigma.*—Shape: Transversely elliptic. Color: RHS 144C.
*Ovary color.*—RHS 143C.

Fruit and seed set: A few seeds develop that are 0.05 cm in diameter and RHS 200A in color.

Disease and insect resistance: No particular resistance or susceptibility to diseases or insects noted to date.

COMPARISON WITH PARENTAL AND COMMERCIAL CULTIVARS

'Keipunes' differs from the female parent, an unnamed proprietary *petunia* plant (unpatented), by having a decumbent plant habit, while the female parent has a spreading plant habit. Additionally, 'Keipunes' has a shorter plant height and a smaller flower diameter than the female parent.

'Keipunes' differs from the male parent, an unnamed proprietary *petunia* plant (unpatented), by having a taller plant height, a larger flower diameter, and a larger plant diameter, than the male parent.

'Keipunes' is similar to the commercial variety 'Revolution Brilliantpink' (U.S. Plant Pat. No. 6,914) however, there are differences as listed in Table 1 below:

TABLE 1

Comparison of Characteristics between 'Keipunes' and 'Revolution Brilliantpink'

| Characteristic | 'Keipunes' | 'Revolution Brilliantpink' |
|---|---|---|
| Blooming period | Late April to late September in Japan | Late March to late September in Japan |
| Inside color of throat | RHS 84A with RHS 79C venation | RHS 74A with RHS 77A venation |
| Main color of corolla tube (outside) | RHS 84A | RHS 70C |
| Flower diameter | 4.5 cm | 7.5 cm |
| Plant height | 4.0 cm | 15.0 cm |
| Stem color | RHS 137B | RHS 144A |
| Leaf length | 4.5 cm | 6.0 cm |
| Leaf width | 1.5 cm | 3.5 cm |
| Leaf color (mature) | Upper surface: RHS 137B<br>Lower surface: RHS 137C | Upper surface: RHS 146A<br>Lower surface: RHS 147B |

TABLE 1-continued

Comparison of Characteristics between 'Keipunes' and 'Revolution Brilliantpink'

| Characteristic | 'Keipunes' | 'Revolution Brilliantpink' |
|---|---|---|
| Leaf color (immature) | Upper surface: RHS 137B<br>Lower surface: RHS 137C | Upper surface: RHS 146A<br>Lower surface: RHS 147B |
| Flower bud length | 1.5 cm | 3.5 cm |
| Flower bud diameter | 0.5 cm | 1.5 cm |
| Petal color (when opening) | Upper surface: RHS 74B<br>Lower surface: RHS 83B | Upper surface: RHS 74A<br>Lower surface: RHS 74A |
| Petal color (fully opened) | Upper surface: RHS 74B<br>Lower surface: RHS 83B | Upper surface: RHS 74A<br>Lower surface: RHS 74A |

TABLE 1-continued

Comparison of Characteristics between 'Keipunes' and 'Revolution Brilliantpink'

| Characteristic | 'Keipunes' | 'Revolution Brilliantpink' |
|---|---|---|
| Peduncle length | 1.5 cm | 2.0 cm |
| Anther color | RHS 92B | RHS 91B |
| Stigma color | RHS 144C | RHS N144D |

We claim:

1. A new and distinct cultivar of *petunia* plant as described and shown herein.

* * * * *